United States Patent
Hedegaard

(10) Patent No.: US 11,357,482 B2
(45) Date of Patent: Jun. 14, 2022

(54) METHOD FOR SAMPLING URINE AND COLLECTOR THEREFORE

(71) Applicant: GPMD ApS, Holstebro (DK)

(72) Inventor: Henning Hedegaard, Sunds (DK)

(73) Assignee: GPMD ApS, Holstebro (DK)

( * ) Notice: Subject to any disclaimer, the term of this patent is extended or adjusted under 35 U.S.C. 154(b) by 808 days.

(21) Appl. No.: 16/318,460

(22) PCT Filed: Jul. 28, 2017

(86) PCT No.: PCT/DK2017/050251
§ 371 (c)(1),
(2) Date: Jan. 17, 2019

(87) PCT Pub. No.: WO2018/019351
PCT Pub. Date: Feb. 1, 2018

(65) Prior Publication Data
US 2019/0223842 A1    Jul. 25, 2019

Related U.S. Application Data

(60) Provisional application No. 62/368,260, filed on Jul. 29, 2016.

(51) Int. Cl.
*A61B 10/00* (2006.01)
*A61F 5/44* (2006.01)

(52) U.S. Cl.
CPC .......... *A61B 10/007* (2013.01); *A61F 5/4404* (2013.01); *A61F 2005/4402* (2013.01)

(58) Field of Classification Search
CPC ................. A61B 10/007; A61F 5/4404; A61F 2005/4402

(Continued)

(56) References Cited

U.S. PATENT DOCUMENTS 3,572,318 A  *  3/1971  Garland ............... A61B 10/007
                                                        604/347
4,445,235 A        5/1984  Slover
(Continued)

FOREIGN PATENT DOCUMENTS

CA       2149598 A1    11/1996
CN     101022764 A      8/2007
(Continued)

OTHER PUBLICATIONS

EasySampler Stool Collection Kit, GP Medical Devices, Apr. 29, 2016.

*Primary Examiner* — Andrew J Mensh
(74) *Attorney, Agent, or Firm* — James Creighton Wray

(57) ABSTRACT

A urine collector (1) and a method for mounting the urine collector to a toilet bowl. The collector is made of paper sheet and comprises a central collection area (20), a front flap (4), a rear part (23), two side wings (3 A, 3B) each extending from the central collection area (20) and further two rear wings (2 A, 2B) extending from the rear part (23). Each of the wings (2 A, 2B, 3 A, 3B) and the front flap (4) are provided with sticky material (6) for fastening them to the toilet bowl (5). The urine collector (1) is mounted onto a toilet bowl (5) by fastening the front flap (4) to the front part of the bowl opening (5C), and fastening the wings (2A, 2B, 3A, 3B) to the edge of the toilet bowl opening (5). After urine collection in the collection area (20), the front flap is detached from the front of the toilet bowl and lifted, while the side wings and rear wings are still attached. This causes the collected urine to flow over the rear part into a separate sampling container.

13 Claims, 3 Drawing Sheets

Figure 1:
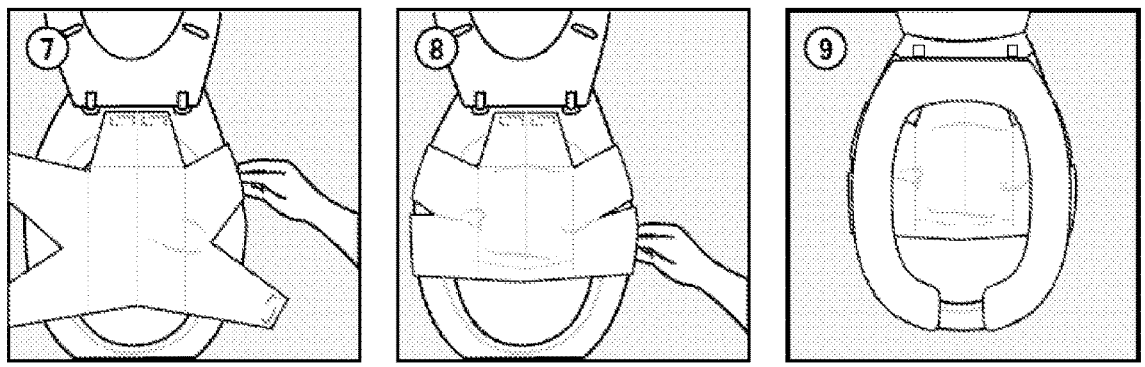

(58) Field of Classification Search
USPC ............ 600/573; 604/332, 347, 317; 4/661, 4/144.1, 484
See application file for complete search history.

(56) References Cited

U.S. PATENT DOCUMENTS

| | | | |
|---|---|---|---|
| 4,975,990 A | | 12/1990 | Chan |
| 5,146,637 A | | 9/1992 | Bressler |
| 5,337,426 A | * | 8/1994 | Matusewicz ....... A61B 10/0038 4/661 |
| 5,412,819 A | | 5/1995 | Matusewicz |
| 5,463,782 A | * | 11/1995 | Carlson ............. A61B 10/0038 4/661 |
| 6,775,852 B1 | * | 8/2004 | Alvarez ............... A61B 10/007 4/144.2 |
| 8,613,711 B2 | | 12/2013 | Babcock |
| 8,615,824 B2 | | 12/2013 | Sonderholm |
| 10,499,886 B1 | * | 12/2019 | Downie ................. G01G 19/52 |
| 2006/0184064 A1 | * | 8/2006 | Paasch ................. A61B 10/007 4/144.1 |
| 2007/0074992 A1 | * | 4/2007 | Fukuda .............. A61B 10/0038 206/528 |
| 2011/0270125 A1 | * | 11/2011 | Sonderholm ...... A61B 10/0038 600/562 |
| 2013/0053729 A1 | | 2/2013 | Stevic-Wages |
| 2018/0317892 A1 | * | 11/2018 | Catlin .................... A47K 11/02 |

FOREIGN PATENT DOCUMENTS

| | | |
|---|---|---|
| DE | 9301299 U1 | 5/1993 |
| DE | 29921867 U1 | 8/2000 |
| DE | 10052879 A1 | 5/2002 |
| EP | 0865254 A1 | 9/1998 |
| EP | 3028646 A1 | 6/2016 |
| WO | 9717019 A1 | 5/1997 |
| WO | 2008080220 A1 | 7/2008 |

* cited by examiner

METHOD FOR SAMPLING URINE AND COLLECTOR THEREFORE

This application claims the benefit of U.S. Provisional Application No. 62/368,260 filed Jul. 29, 2016 and PCT/DK2017/050251 filed Jul. 28, 2017, International Publication No. WO2018/019351, which are hereby incorporated by reference in their entirety as if fully set forth herein.

FIELD OF THE INVENTION

The present invention relates to a method for collecting urine and a collector therefore.

BACKGROUND OF THE INVENTION

Urine samples are widely used for screening and diagnosing in the field of medicine as well as for doping control at sports events and drug control in police custody. Sampling urine from a patient has to be easy, reliable, and hygienic. Furthermore, it is often desired that the production price is low and waste material small and the product environmentally friendly.

Urine collection in custody service is disclosed in US patent application No. 2013/0031030. The collector is a disposable plastic bag large enough to cover the toilet seat entirely and with a depression for collecting the entire urine volume. From the collector, a sample is taken into a sample cup for testing. The transfer procedure is not explained in detail in the disclosure, but it can be expected that the sampling makes it difficult to avoid urine on the outer side of the cup, which implies non-hygienic moments. Also, it appears to require some difficult handling of the collector in order to get it emptied. Furthermore, the plastic has to be discarded, and tend to smell if kept in a waste container for more than a few hours. Also, the polyethylene polymer material is not environmentally friendly. All in all, the collector does not fulfil the requirements to a modern urine sampling product.

A urine collector for a male child is disclosed in U.S. Pat. No. 7,996,926, the collector hanging on the outer side of the toilet bowl and being provided at a lower level.

A more complicated device is disclosed in U.S. Pat. No. 5,060,317, which is not fulfilling the requirements for minimizing waste material.

For stool sampling, the corresponding products appear to have undergone a more pronounced development and practical products have been provided for such sampling. Special focus is on avoiding mix of urine with the stool, why the products are designed to avoid urine or to drain urine from stool. Examples are disclosed in U.S. Pat. Nos. 8,615,824; 8,613,711; 5,463,782; 5,412,819; 5,337,426, 4,445,235, 4,975,990; US patent application US2007/074992, European patent application EP3028646 and EP0865254, and German patent application DE10052879.

A further prior art stool collector is shown in FIG. 1, which is marketed under the trade name EasySampler by GP Medical Devices ApS, also marketed by Alpco and disclosed on www.Alpco.com.

It would be desirable to provide an improved urine sampling method and product.

DESCRIPTION/SUMMARY OF THE INVENTION

It is therefore the objective of the invention to provide an improvement in the art. In particular, it is an objective of the invention to provide improved urine collection and a urine collector which is easy to use, reliable, and hygienic, for which the production price is low and amount of waste material small. It is also an objective that it is environmentally friendly. These objectives are obtained with a urine collector as described in detail in the following. Also described is a method for sampling urine with it.

A urine collector is provided as a flexible sheet, for example a water-defibratable paper sheet or a biodegradable polymer or starch sheet, especially water soluble product. Thus, when the sheet is flushed out of the toilet bowl with water, it defibrates or disintegrates similarly to toilet paper. Thus, the sheet being is environmental friendly.

The sheet, when lying flat in a plane, has a front edge region and an opposite rear edge region and two opposite side edge regions between the front edge region and the rear edge region. The terms front, rear and sides are defined relatively to the parts of a toilet bowl to which the respective regions are fastened, as will become more apparent in the following.

The sheet comprises a central collection area, a front flap extending forward from the central collection area, and a rear part extending rearward from the central collection area, and two side wings of which each one is extending sideways in opposite directions outward from the central collection area between the front flap and the rear part. Further, two rear wings extend sideways from the rear part in opposite directions. Each of the rear wings, side wings, and front flap are provided with sticky material for fastening them to the toilet bowl.

For mounting the urine collector onto a toilet bowl, the method comprises fastening the front flap to the front of the toilet bowl, fastening the side wings to an edge of the toilet bowl in a front half of the toilet bowl, and fastening the rear wings to the edge of the toilet bowl towards the rear of the toilet bowl relatively to the side wings, for example to the edge of a rear half of the toilet bowl. During this mounting, the construction of the urine collector assists automatically in positioning the collection area as the lowest part of the urine collector in the toilet bowl. After this mounting, the urine collector is ready for collection of urine.

After collecting urine in the collection area, only the front flap is detached from the front of the toilet bowl and is lifted gently and slightly for elevating the collection area relatively to the rear part while the side wings and rear wings are still attached to the toilet bowl. Alternatively, the front flap is lifted by fingers without detaching it. This causes the collected urine to flow over the rear part into a sampling container, for example a bottle or cup, which is provided separate from the sheet at the rear part. This way, a volume of urine is sampled in the sampling container. In practice, it has turned out that the urine collector deforms automatically into a shape with a central hollow for controlled flow of urine towards the rear for collection. Only after the sampling, the side wings and the rear wings are detached from the toilet bowl and flushed out of the toilet bowl together with the flushing water.

Optionally, the rear part comprises an opening for collection of a urine sample by flow of urine from the urine collection area and through the opening.

The urine collector is elongate and comprises a central longitudinal line. Advantageously, the urine collector is symmetrical about the central longitudinal line and, optionally, comprises a central longitudinal folding extending along this line and through the rear part as a groove for flow of urine along the groove. Lifting the front flap causes a flow of urine from the collection area and along the central longitudinal line, for example along and inside the groove of the folding. Urine is then collected into the sample container at an end of the central longitudinal folding.

For example, the rear part comprises an opening around the central longitudinal folding, and flow of urine from the collection area along and inside the central longitudinal folding by lifting the front flap will result in the urine flowing out of the urine collector from the groove and through the opening.

In a practical embodiment, the central collection area is enclosed by a rear folding and a front folding and two side foldings. The rear folding extends laterally to the front part or the rear part, or both.

For example the rear folding extends across the central longitudinal line, optional folding, between opposite notches, each of the opposite notches being provided between a front edge of the rear wing and a rear edge of the side wing.

The front folding extends laterally across the central longitudinal line, optionally folding, for example from a front edge of one of the two side wings to a front edge of the other of the two side wings. Typically, the side foldings are parallel with the central longitudinal line where one of each side folding is provided on either side of the longitudinal line, optional folding.

In advantageous embodiments, the rear folding defines a border between the urine collection area and the rear part for elevation of the rear part relatively to the urine collection area when mounted on a toilet bowl. As already indicated above, the rear part, optionally, comprises an opening on the central longitudinal line, optional folding, for collection of a urine sample by flow of urine from the urine collection area along the central longitudinal line, optionally folding, and through the opening.

For example, the front folding defines a border between the urine collection area and the front flap for elevation of the front flap relatively to the urine collection area when mounted on a toilet bowl.

Optionally, rectangular transition regions are provided symmetrically, with one transition region on either side of the central longitudinal line, optional folding. Each transition region extends from the front flap to one of the front edges of the side wings. Advantageously, each transition region has a diagonal fold extending from the front fold at a corner of the urine collection area outwards and towards the front edge region.

For example, the thickness of the sheet is less than 0.1 mm, optionally less than 0.06 mm. An exemplary weight of the sheet material is between 40 and 80 grams per square meter.

Some useful examples and parameters of paper material for the urine collector are given in the following.
  a longitudinal pull strength of at least 1.5, for example between 1.5 and 4.6, according to the SCAN P-67 standard,
  a longitudinal tear strength of at least 125, for example between 125 and 350, according to the ISO 1974 standard,
  a transversal pull strength of at least 0.7, for example between 0.7 and 2.0, according to the SCAN P-67 standard,
  a transversal tear strength of at least 210, for example between 210 and 450, according to the ISO 1974 standard.

For example, the paper type is in accordance with the ISO 536 standard, implying that when flushed through the toilet into a sewage system the paper attains defibrillation within less than 20 minutes, for example within 8 to 12 minutes, when in contact with the moving water of the sewage system during normal circulation through a common sewage system.

SHORT DESCRIPTION OF THE DRAWINGS

Figure 2:
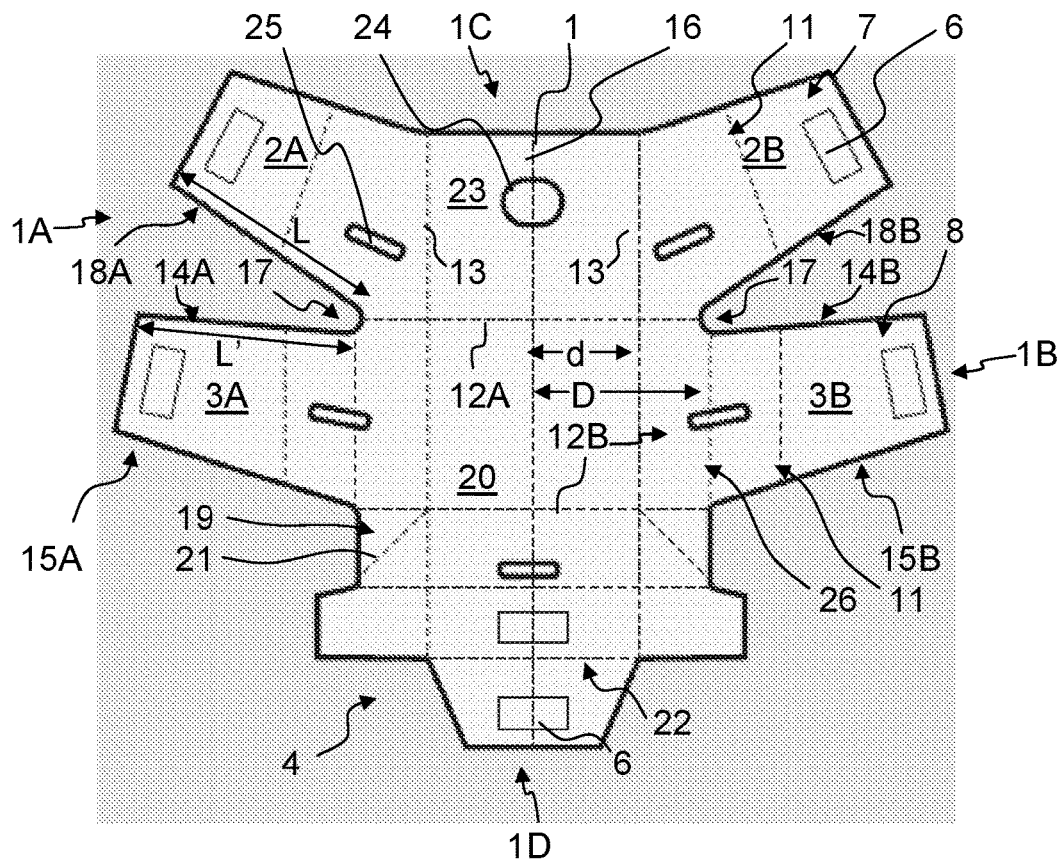
Figure 3:
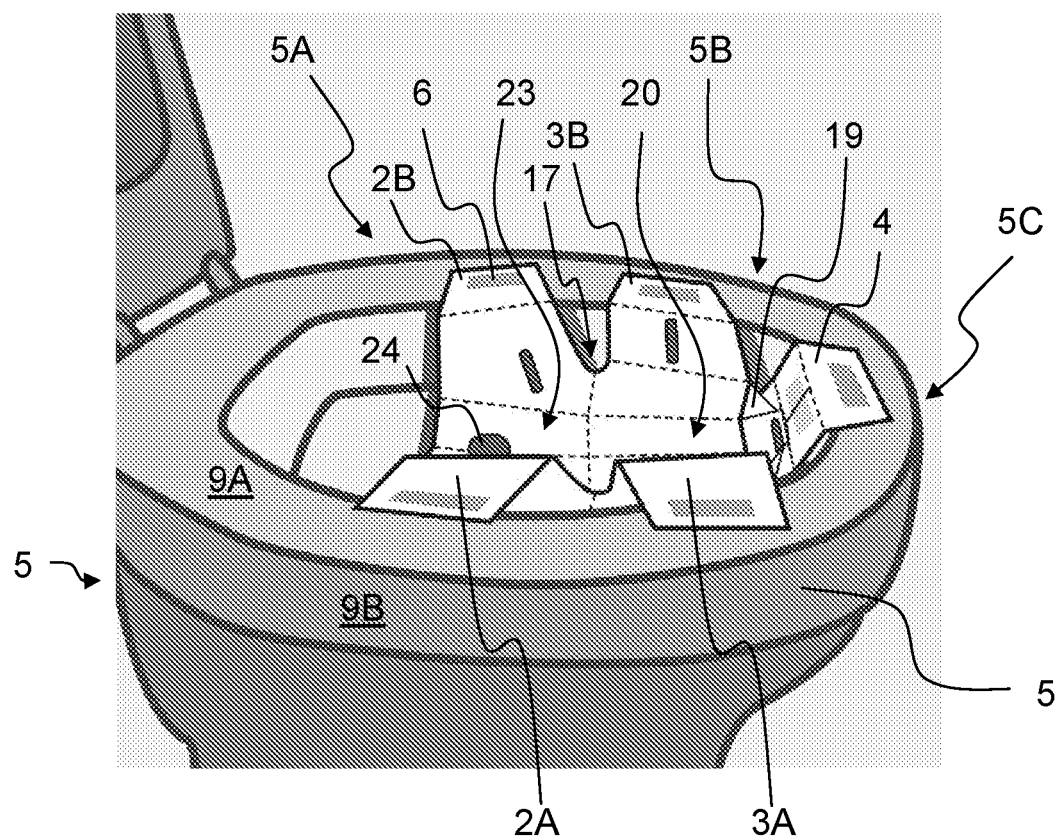
Figure 4:
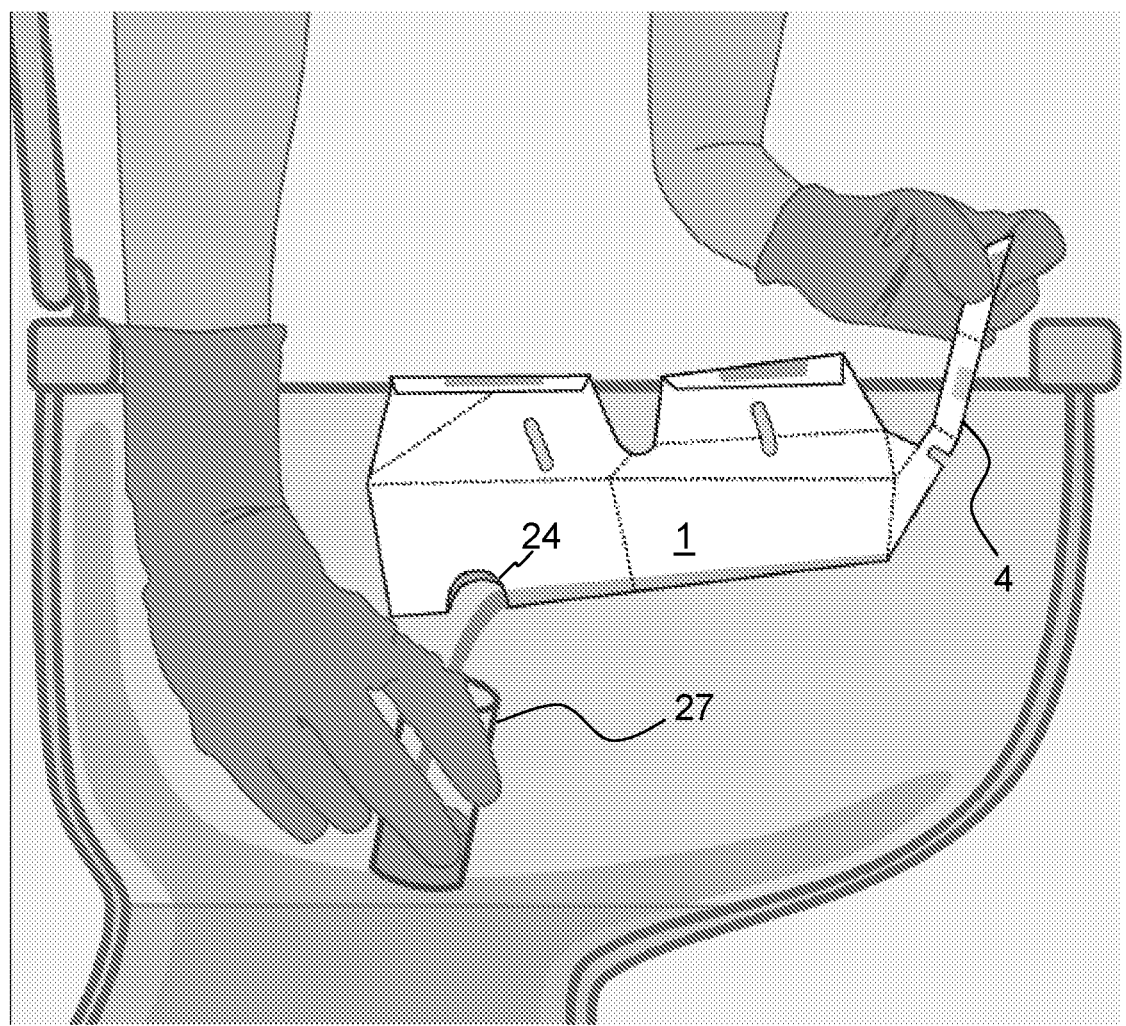

The invention will be explained in more detail with reference to the drawing, where
  FIG. 1 shows a prior art stool collector
  FIG. 2 illustrates a urine collector;
  FIG. 3 shows the mounted urine collector in perspective on the toilet bowl;
  FIG. 4 is an illustration of urine sampling.

DETAILED DESCRIPTION/PREFERRED EMBODIMENT

FIG. 1 illustrates a stool collector according to the prior art, which is mounted on a toilet bowl. In order to avoid urine, the front part of the toilet bowl is not covered by the stool collector.

FIG. 2 illustrates a urine collector 1 when flat and unfolded, and FIG. 3 is a perspective view of the urine collector 1 mounted on a toilet bowl 5.

The urine collector 1 comprises two rear wings 2A, 2B that are mounted on a rear half 5A of a toilet bowl 5 and two side wings 3A, 3B that are mounted on the front half 5B of the toilet bowl 5, and a front flap 4 that is mounted on the front part 5C of the toilet bowl 5. When comparing with the prior art of FIG. 1, the mounting procedure is largely circumvented as compared to the mounting procedure of the prior art stool collector.

However, apart from the difference in orientation of the urine collector 1 in FIG. 3 as compared to the prior art stool collector in FIG. 1, there is also a difference in that sticky material 6 in end regions 7 of the rear wings 2A, 2B and the end regions 8 of the side wings 3A, 3B are fastened to the top edge 9A of the toilet bowl 5 in contrast to the fastening of corresponding sticky tape 6 to the sides 9B of the toilet bowl in the prior art stool collector in FIG. 1. The fastening to the top edge 9A of the toilet bowl 5 of the rear wings 2A, 2B and the side wings 3A, 3B has the advantage that the urine collector can extend relatively deep into the toilet bowl 5 while at the same time minimizing the necessary material therefore. The former has the advantage of a relatively large collection volume, and the latter has the advantage of minimizing waste.

The urine collector 1 comprises a number of folding lines shown as stippled lines, which in combination are more complex and sophisticated than in the prior art stool collector of FIG. 1. Folding lines are provided in the urine collector 1 prior to mounting on the toilet bowl 5 and are part of the urine collector 1 product when sold to users.

First foldings 11 are provided close to the region of the sticky material 6 in order to direct a central collection area 20 deep into the bowl 5. The rear wings 2A, 2B have a front edge 18A, 18B with a length L, and the side wings 3A, 3B have a rear edge 14A, 14B with a length L'. The front edge 18A of the rear wing 2A and the rear edge 14A of the side wing 3A form a notch 17. The first folding 11 is provided at a distance which is between ¼ and ¾ of the length L and L', respectively. In other words, the first folding is provided across the central half of the rear wings 2A, 2B and the side wings 3A, 3B. Optionally, and as shown, in the rear wing 2A, 2B, the first folding line 11 is provided at a distance which is between ⅓ and ⅔ of L. In other words, it is provided across the central third of the rear wings 2A, 2B.

The urine collector 1 is symmetrical about a central longitudinal line 16. An optional central longitudinal folding extends along this line 16. The central longitudinal folding when mounted correctly is directed downwards in order to function as a downward directed groove for flow of urine within that groove.

The central collection area 20 is enclosed by a rear folding 12A and a front folding 12B and two straight side foldings 13. The side foldings 13 extend from the rear edge 1C to the front edge 1D of the urine collector 1 and are parallel to the central longitudinal line 16, optional folding, on either side of the central longitudinal line 16 at a distance d from the central longitudinal line 16. The rear folding 12A and front folding 12B are perpendicular thereto. The rear folding 12A extends between opposite notches 17 on either side of the central longitudinal line 16, optional folding. Each notch 17 is provided between a side wing 3A, 3B and a rear wing 2A, 2B and, thus, adjacent to the rear edges 14A, 14B of the side wings 3A, 3B. The front folding 12B extends from a front edge 15A of one of the two side wings 3A to a front edge 15B of the other of the two side wings 3B.

This configuration is different from the prior art as in FIG. 1, in which there is not provided such rear folding 12A across the central longitudinal line 16, optional folding, from opposite notches 17, each being provided between a side wing 3A, 3B and a rear wing 2A, 2B. In contrast thereto, the prior art stool collector according to FIG. 1 comprises a rear folding which is placed remote from notches between rear and side wings. The advantage of the urine collector 1 having such rear folding 12A implies that the central collection area 20 extends deeper into the bowl 5 as compared to the prior art stool collector of FIG. 1.

The side foldings 13 are parallel with the central longitudinal line 16 and provided at a first distance d from the central longitudinal line 16, optional folding. This first distance d is smaller than a second distance D, where the second distance D is a lateral distance from the front edge 15A, 15B of the side wing 3A, 3B to the central longitudinal line 16, optional folding.

When comparing the prior art stool collector in FIG. 1 with the urine collector of FIG. it is readily seen that the overall shape is very different. For example, the front edges 18A, 18B of the rear wings 2A, 2B, and the front edges 15A, 15B of the side wings 3A, 3B all form an acute angle towards the rear edge 1C and in a direction away from the front flap 4. In the prior art stool collector in FIG. 1 the corresponding edges of the two pairs of wings are directed oppositely, namely only one set of wings forming an acute angel with a rear or front edge region.

It is also readily recognised that the front flap 4 is broader than the distance of 2d between the side foldings 13. In the stool collector of FIG. 1, the extending flap on the rear of the toilet bowl is narrower than the distance between side foldings.

As compared to the prior art in FIG. 1, also the front flap 4 is different. The front flap 4 extends from the front edges 15A, 15B of the side wings 3A, 3B in a forward direction to the front 5C of the toilet bowl 5 when mounted. The front flap 4 bends upwards from the central collection area 20 due to the second folding 2A extending between the front edges 15A, 15B of the side wings.

All these features individually and in common contribute to as successful urine collector 1 due to the urine collection area 20 being lowest and easy to mount and handle for urine collection.

As the third foldings 13 have a distance d closer to the central longitudinal line 16, optional folding, than the distance D from the central longitudinal line 16, optional folding, to the side wings 3a, 3B, a transition region 19 is provided on each side from the front flap 4 to the front edge 15A, 15B of the side wings 3A, 3B, where each transition regions 19 has a diagonal fold 21. The transition region 19 is best seen in FIG. 3. It prevents the urine from unintentionally running out of the urine collection area 20.

The second folding 12A between the notches 17 defines a line from which a rear part 23 of the urine collector 1 is folded upwards. This results in the central collection area 20 being located deepest between the rear part 23 and the front flap 4, which is best seen in FIG. 3. For larger collection volumes, for example larger than 100 ml or larger than 200 ml, for example up to 400 ml, the notches 17 could be provided with a folded transition region similar to the transition region 19.

The rear part 23 is provided with an opening 24 located on the central longitudinal line 16, optional folding. The opening 24 is used for easy emptying of the central collection area 20, once urine has been collected in it. For emptying, the front flap 4 is, typically, detached from the front 5C of the toilet bowl 5 and gently lifted so that the urine flows towards and into the rear part 23. From the rear part 23, it leaves the urine collector 1 through the opening 24. It is also possible to lift part of the front flap without detaching it. Personnel collecting urine would, thus, locate a sample container (not shown) underneath the opening 24 and collect the urine while easily preventing contact with the urine on the hand or on the outer side of the sample container 27, which is a situation illustrated in FIG. 4.

After urine collection, the urine collector 1 is discarded into the toilet 5 and flushed out.

For example, the material of the urine collector 1 is paper of the type that defibrillates in water. Alternatively, the material is biodegradable polymer or starch, especially water soluble materials. Thus, when the sheet is flushed out of the toilet bowl with water, it defibrates or disintegrates similarly to toilet paper. The sticky material 6 on the urine collector 1 is water soluble.

For minimizing the risk for the sheet being prevented from flushing due to air collecting in the sheet, it is provided with a number of flush holes 25, one on each of the rear wings 2A, 2B, side wings 3A, 3B, and front flap 4.

Optionally, the urine collector 1 also comprises a fourth folding line 26 at a distance D from the central longitudinal line 1616 and parallel with the central longitudinal line 16, optional folding, and extending from the notch 17 so as to define an onset of the side wings 3A, 3B.

REFERENCE NUMBERS 1 urine collector
2A, 2B rear wings
3A, 3B side wings
4 front flap
5 toilet bowl
5A rear half of toilet bowl 5
5B front half of toilet bowl 5
5C front of toilet bowl 5
6 sticky tape regions
7 end regions 7 of the rear wings 2A, 2B
8 end regions of the side wings 3A, 3B
9A top edge of the toilet bowl 5
9B sides of the toilet bowl
11 first foldings on rear wings 2A, 2B and side wings 3A, 3B 12A rear folding
12B front foldings
13 side foldings
14A rear edge of one of the two side wings 3A
14B rear edge of the other side wing 3B
15A front edge of one of the two side wings 3A
15B front edge of the other side wing 3B
16 central longitudinal line, optional folding
17 notch between rear wings 2A, 2B and side wings 3A, 3B
18A, 18B front edges of rear wings 2A, 2B
19 transition region from front flap 4 to front edge 15A, 15B or side wings 3A, 3B
20 central collection area
21 diagonal folding in transition region 19
22 front flap fold
23 rear part of urine collector 1
24 opening in rear part
25 flush holes
26 fourth folding lines at distance D from central longitudinal line 16
27 sampling container

The invention claimed is:

1. A method for collecting urine, the method comprises providing a urine collector (1) made of a flexible sheet, the sheet comprising a central collection area (20), a front flap (4) extending forward from the central collection area (20), and a rear part (23) extending rearward from the central collection area (20), each of two side wings (3A, 3B) extending sideways outward from the central collection area (20) between the front flap (4) and rear part (23), two rear wings (2A, 2B) extending sideways from the rear part (23); each of the rear wings (2A, 2B), side wings (3A, 3B), and front flap (4) being provided with sticky material (6); the method comprising with the sticky material, respectively, fastening the front flap to the front (5C) of the toilet bowl (5), fastening the side wings (3A, 3B) to an edge of the toilet bowl (5) in a front half (5B) of the toilet bowl (5), and fastening the rear wings (2A, 2B) to the edge of the toilet bowl (5) towards the rear of the toilet relatively to the side wings; positioning the collection area (20) as the lowest part of the urine collector (1); collecting urine in the collection area (20); detaching only the front flap (4) from the front (5C) of the toilet bowl (5) and lifting the front flap (4) for elevating the collection area (20) relatively to the rear part (23) and causing the collected urine to flow over the rear part (23) into a sampling container provided separate from the sheet at the rear part (23) and sampling a volume of urine in the sampling container; detaching the side wings (3A, 3B) and the rear wings (2A, 2B) from the toilet bowl (5) and flushing the urine collector (1) out of the toilet bowl (5).

2. The method according to claim 1, wherein the rear part (23) comprises an opening (24) and the method comprises causing a flow of urine from the collection area (20) to the rear part (23) to the opening (24) and through the opening (24) by lifting the front flap (4) and collecting urine from the opening (24).

3. The method according to claim 2, wherein the urine collector (1) is symmetrical about a central longitudinal line, wherein the opening (24) is provided on the central longitudinal line and wherein the method comprises causing a flow of urine from the collection area (20) to the rear part (23) to the opening (24) along the central longitudinal line and through the opening (24) by lifting the front flap (4) and collecting urine from the opening (24).

4. The method according to claim 1, wherein the urine collector (1) is symmetrical about a central longitudinal line (16) and comprises a central longitudinal folding along the central longitudinal line (16) and through the rear part (23) as a groove for flow of urine along the groove; and wherein the method comprises causing a flow of urine from the collection area (20) along the groove by lifting the front flap (4) and collecting urine from the groove.

5. A urine collector for collecting urine in a toilet bowl, the urine collector being made of a flexible sheet, the sheet comprising a central collection area (20), a front flap (4) extending forward from the central collection area (20), and a rear part (23) extending rearward from the central collection area (20), each of two side wings (3A, 3B) extending sideways outward from the central collection area (20) between the front flap (4) and rear part (23), two rear wings (2A, 2B) extending sideways from the rear part (23); each of the rear wings (2A, 2B), side wings (3A, 3B), and front flap (4) being provided with sticky material for fastening the front flap to the front (5C) of the toilet bowl (5), for fastening the side wings (3A, 3B) to an edge of the toilet bowl in a front half of the toilet bowl, and for fastening the rear wings (2A, 2B) to the edge of the toilet bowl towards the rear of the toilet bowl relatively to the side wings, while the central collection area (20) is located as the deepest part of the urine collector (1); wherein the central collection area (20) is enclosed by a rear folding (12A) and a front folding (12B) and two side foldings (13); wherein the rear folding (12A) is extending from one to another of two opposite notches (17) on opposite sides of the urine collector (1), each of the opposite notches (17) being provided between a front edge (18A, 18B) of the rear wing (2A, 2B) and a rear edge (14A, 14B) of the side wing (3A, 3B); the front folding (12B) extending from a front edge (15A) of one of the two side wings (3A) to a front edge (15B) of the other side wing (3B); and wherein the rear part (23) comprises an opening (24) for collection of a urine sample by flow of urine from the urine collection area (20) to the rear part (23) to the opening (24) and through the opening (24).

6. The urine collector according to claim 5 wherein the front folding (12B) defines a border between the urine collection area (20) and the front flap (4) for elevation of the front flap (4) relatively to the urine collection area (20) when mounted on a toilet bowl (5).

7. The urine collector according to claim 6, wherein the side foldings are lateral to the front folding (12B).

8. The urine collector according to claim 5, wherein the rear folding (12A) defines a border between the urine collection area (20) and the rear part (23) for elevation of the rear part (23) relatively to the urine collection area (20) when mounted on a toilet bowl (5).

9. The urine collector according to claim 6, wherein the urine collector (1) is symmetrical about a central longitudinal line (16).

10. The urine collector according to claim 9, wherein the opening (24) is provided on the central longitudinal line (16).

11. The urine collector according to claim 9, wherein the sheet when lying flat in a plane has a front edge region (1D) and an opposite rear edge region (1C) and two side edge regions (1A, 1B) between the front edge region (1D) and the rear edge region (1C), wherein two rectangular transition regions (19) are provided symmetrically on either side of the central longitudinal line (16), each transition region (19) extending from the front flap (4) to one of the front edges (15A, 15B) of the side wings (3A, 3B), where each transition regions (19) has a diagonal fold (21) extending from the front fold (2B) at a corner of the urine collection are (20) outwards and towards the front edge (1D) region.

12. The urine collector according to claim 5, wherein the front edges (18A, 18B) of the rear wings (2A, 2B), and the front edges (15A, 15B) of the side wings (3A, 3B) all form an acute angle towards the rear edge (1C) and in a direction away from the front flap (4).

13. The urine collector according to claim 9, wherein the sheet comprises a central longitudinal folding extending along the central longitudinal line (16) and through the rear part (23) as a groove for flow of urine along the groove.

* * * * *